(12) United States Patent
Fritz et al.

(10) Patent No.: US 8,920,412 B2
(45) Date of Patent: Dec. 30, 2014

(54) ELECTROSURGICAL GENERATOR FOR THE TREATMENT OF A BIOLOGICAL TISSUE, METHOD FOR REGULATING AN OUTPUT VOLTAGE OF AN ELECTROSURGICAL GENERATOR, AND CORRESPONDING USE OF THE ELECTROSURGICAL GENERATOR

(75) Inventors: Martin Fritz, Tübingen (DE); Heiko Schall, Nürtingen (DE)

(73) Assignee: ERBE Elektromedizin GmbH, Tuebingen (DE)

( * ) Notice: Subject to any disclaimer, the term of this patent is extended or adjusted under 35 U.S.C. 154(b) by 1031 days.

(21) Appl. No.: 13/002,145

(22) PCT Filed: Jun. 3, 2009

(86) PCT No.: PCT/EP2009/003964
§ 371 (c)(1),
(2), (4) Date: Dec. 30, 2010

(87) PCT Pub. No.: WO2010/000362
PCT Pub. Date: Jan. 7, 2010

(65) Prior Publication Data
US 2011/0112526 A1    May 12, 2011

(30) Foreign Application Priority Data

Jun. 30, 2008  (DE) .......................... 10 2008 030 876
Aug. 19, 2008  (DE) .......................... 10 2008 038 314

(51) Int. Cl.
| | |
|---|---|
| *A61B 18/18* | (2006.01) |
| *A61B 18/12* | (2006.01) |
| *A61B 18/00* | (2006.01) |
| *A61B 18/04* | (2006.01) |

(52) U.S. Cl.
CPC ... *A61B 18/1206* (2013.01); *A61B 2018/00767* (2013.01); *A61B 2018/00892* (2013.01); *A61B 2018/00827* (2013.01); *A61B 18/042* (2013.01)
USPC .............................................. 606/40; 606/34

(58) Field of Classification Search
CPC .. A61B 18/042; A61B 18/12; A61B 18/1206; A61B 18/1233; A61B 2018/00583; A61B 2018/00636; A61B 2018/00648; A61B 2018/00666; A61B 2018/0069; A61B 2018/00696; A61B 2018/00702; A61B 2018/00708; A61B 2018/0072; A61B 2018/00767; A61B 2018/00773; A61B 2018/00827; A61B 2018/00892; A61B 2018/00898; A61B 2018/1213
USPC ..................................................... 606/32–41
See application file for complete search history.

(56) References Cited

U.S. PATENT DOCUMENTS

| | | | |
|---|---|---|---|
| 5,423,808 A | 6/1995 | Edwards et al. | |
| 2003/0153908 A1* | 8/2003 | Goble et al. ................... | 606/41 |

(Continued)

FOREIGN PATENT DOCUMENTS

| | | |
|---|---|---|
| CN | 101170958 A | 4/2008 |
| DE | 25 04 280 A1 | 8/1976 |

(Continued)

OTHER PUBLICATIONS

Elmar Schrüfer, Elektrische Messtechnik. 1. Auflage, München [u-a]: Hanserverlag, 1983, Seiten 54-56, 62-65. ISBN 3-446-13812-9.

*Primary Examiner* — Linda Dvorak
*Assistant Examiner* — Amanda Scott
(74) *Attorney, Agent, or Firm* — Dickstein Shapiro LLP

(57) ABSTRACT

An electrosurgical generator for the treatment of biological tissue. The electrosurgical generator comprises a generator part which supplies a high-frequency ("HF") treatment current with an HF voltage set according to a voltage control signal. A measuring device detects the HF treatment current and the HF voltage and generates corresponding current and voltage signals. The current signal and the voltage signal are fed to a conversion device which forms a real current signal corresponding to the real component of the HF treatment current. A regulation device compares the real current signal with a pre-settable target value and generates the voltage control signal on the basis of the comparison. The real component of the treatment current is determined and the generator part is adjusted so that said real component approximates to a pre-determined target value.

12 Claims, 2 Drawing Sheets

(56) References Cited

U.S. PATENT DOCUMENTS

2005/0113819 A1* 5/2005 Wham et al. .................... 606/34
2007/0233058 A1  10/2007 Beller

FOREIGN PATENT DOCUMENTS

| | | |
|---|---|---|
| EP | 0 495 140 B1 | 7/1992 |
| EP | 1 554 985 A1 | 7/2005 |
| EP | 1 693 014 A1 | 8/2006 |
| EP | 1 707 144 A1 | 10/2006 |
| JP | 2-283363 A | 11/1990 |
| JP | 2006-255405 A | 9/2006 |
| WO | WO 00/12019 A1 | 3/2000 |
| WO | WO 2005/046496 A1 | 5/2005 |
| WO | WO 2006/119892 A1 | 11/2006 |

* cited by examiner

ELECTROSURGICAL GENERATOR FOR THE TREATMENT OF A BIOLOGICAL TISSUE, METHOD FOR REGULATING AN OUTPUT VOLTAGE OF AN ELECTROSURGICAL GENERATOR, AND CORRESPONDING USE OF THE ELECTROSURGICAL GENERATOR

FIELD

The disclosure relates to an electrosurgical generator for the treatment of biological tissue, a method for regulating an output voltage of an electrosurgical generator and corresponding use of said electrosurgical generator.

BACKGROUND

A known problem in high frequency surgery is the reproducibility and consistency of quality of cutting and/or coagulation processes. It is known that the quality of these processes depends substantially on the high frequency voltage used therefor and on the intensity of the electric arc between the active electrode and the tissue. However, with contactless coagulation processes, these variables are influenced, inter alia, by the distance of the instrument used from the tissue. It is therefore desirable to provide a coagulation device and a corresponding method which produce a constant arc regardless of said distance.

A further problem lies in improving the ignition behaviour of the electrosurgical devices. This applies, in particular, to electrosurgical instruments that generate an inert gas plasma. It is therefore desirable to ensure reliable ignition of the plasma, regardless of distance, within particular limits (e.g. 0 mm to 30 mm). In addition, for safety reasons, a limitation of the current flow is desirable.

It is known from EP 0 495 140 B1 to detect the real component of the treatment current generated by an HF (high-frequency) generator with a suitable real current sensor. A current control device processes this variable and limits the maximum current level. In a further exemplary embodiment, the current control device switches the HF generator off if the measured current reaches or exceeds the pre-set maximum current level. By determining the real component of the current, it is ensured that unwanted leakage currents are not additionally and erroneously taken into account, which could lead to undesirable switching off of the device.

From DE 25 04 280, an HF generator for an electrosurgical instrument is known which has a control device which regulates the power of the HF generator. This regulation is carried out based on the detection of an arc generated by the HF treatment current. For this purpose, the control device has suitable sensors.

A high frequency device for generating a plasma arc for the treatment of a biological tissue is known from WO 00/12019. Here, too, the power of the generator is limited by a control device, particularly a suitably configured regulating circuit. The regulating circuit of WO 00/12019 is imprecise and very complex.

SUMMARY

It is an object of the present disclosure to provide an improved electrosurgical generator for the treatment of biological tissue. In particular, an electrosurgical generator is to be provided which has improved ignition behaviour and improved reproducibility in the treatment results. Furthermore, a corresponding method and a corresponding use are provided.

These aims are achieved with an electrosurgical generator for treatment by, for example, cutting or coagulation of biological tissue, comprising
a generator part which supplies an HF treatment current with an HF voltage set according to a voltage control signal such that electrical energy can be supplied to the biological tissue;
a measuring device for detecting the HF treatment current and the HF voltage and for generating a corresponding current signal and a corresponding voltage signal;
a conversion device to which the current signal and the voltage signal are fed and which is configured such that a real current signal corresponding to the real component of the HF treatment current is formed from the current signal and the voltage signal; and
a regulation device which compares the real current signal with a pre-settable target value and generates the voltage control signal on the basis of the comparison,
so that the real component of the HF treatment current is adjustable according to the target value.

The present disclosure therefore provides for calculation of the actual real component of the HF treatment current and, based thereon, for an adjustment of the voltage control signal, so that possible target values can be adjusted and maintained. This opens up many application possibilities. In the first place, predetermined coagulation or cutting modes which presuppose a particular frequency or a particular power level can be precisely maintained. In addition, the ignition procedure can be made significantly more reliable for contactless coagulation procedures. The ignition and the treatment carried out by means of the corresponding instrument are independent of the distance between the tissue and the electrode of the instrument.

The electrosurgical generator can comprise a power limiting device which detects a real power based on the current signal and the voltage signal and limits these to a pre-set value. Power limitation therefore takes place depending on the real power, which depends on the limit conditions. Factors taken into account include, in particular, the distance between the electrodes and/or between the electrodes and the tissue, the instrument used, the electrode size, etc.

The electrosurgical generator can comprise a current limiting device, which limits the real component of the treatment current to a pre-set value. Preferably, therefore, power limitation is carried out based on the adjustment of the current.

The electrosurgical generator can comprise a data input and/or a storage device for input and storage of real resistance components and/or reactive impedance components of attached surgical instruments and loads, wherein the data input device and/or the storage device is connected to the conversion device, wherein the conversion device is configured to include the reactive impedance components when calculating the real component of the HF treatment current.

Therefore, when the real component of the HF treatment current is calculated, the type of electrosurgical device, in particular the specific real resistance component and/or the reactive impedance component can be taken into account. It is advantageous if a combination of the real resistance components and the reactive impedance components is stored. Furthermore, cables and lines that are used together with the respective instruments and cable lengths can be taken into account. Physical variables that can be stored in a data input and/or storage device of this type are: resistance (R), inductance (L) and capacitance (C).

The conversion device can comprise a computer device which forms the real current signal, making use of one of the following alternatives:
a Hilbert transform;
a discrete Fourier transform (DFT);
a fast Fourier transform (FFT); and
formation of a mean power,
from (N) sample values:

$$P = \frac{1}{N}\sum_{k=1}^{N} u(k) \cdot i(k)$$

and formation of effective values of voltage and current:

$$u_{\mathit{eff}} = \frac{1}{N}\sqrt{\sum_{k=1}^{N}(u(k))^2}$$

$$i_{\mathit{eff}} = \frac{1}{N}\sqrt{\sum_{k=1}^{N}(i(k))^2}$$

and of a power factor:

$$\cos\varphi = \frac{P}{u_{\mathit{eff}} \cdot i_{\mathit{eff}}}$$

so that the real current signal is given by:

$i_{real,\mathit{eff}} = i_{\mathit{eff}} \cdot \cos\varphi$.

The calculation device can therefore calculate the real current signal in advantageous manner. Modern digital signal processors are configured so that calculation of the corresponding values, particularly the real current signal, can be performed in real time. Complex signal processing operations can thus also be carried out without causing any delay in the regulation of the HF treatment current. The Hilbert transform and the fast Fourier transform, as well as said formation of a mean power are suitable for calculating the real component of the HF treatment current in a way that is both useful and error-tolerant. If, in particular, the method is used to calculate the real current using the effective values, an implementation which saves computing resources can be assured. The method requires relatively few operations in order to determine the real component. A suitable regulation loop can therefore be run through more often, with the result that more precise, faster regulation of the treatment current can be achieved.

The problem addressed is also solved with a method for regulating an output voltage of an electrosurgical generator which supplies an HF treatment current at an HF voltage for treatment of biological tissue. The method comprises the following steps:
detecting the HF treatment current and the HF voltage and generating a corresponding current signal and a corresponding voltage signal;
forming a real component of the HF treatment current from the current signal and the voltage signal and generating a corresponding real current signal;
comparing the real current signal with a pre-settable target value and generating a voltage control signal based on the comparison; and
regulating the output voltage such that the real component of the HF treatment current corresponds to the target value.

The method has similar advantages to the device disclosed above.

The method can calculate the real current signal making use of one of the following alternatives:
a Hilbert transform;
a discrete Fourier transform (DFT);
a fast Fourier transform (FFT); and
formation of a mean power via the determination of real values (see above).

The method is particularly suitable for calculating the treatment current for applications with plasma gas.

The problem is also solved by the use of said electrosurgical generator.

BRIEF DESCRIPTION OF THE DRAWINGS

The disclosure will now be described by reference to some exemplary embodiments, illustrated by the drawings, in which.

DETAILED DESCRIPTION

In the description that follows, the same reference signs are used for similar and similarly acting parts.

Figure 1:
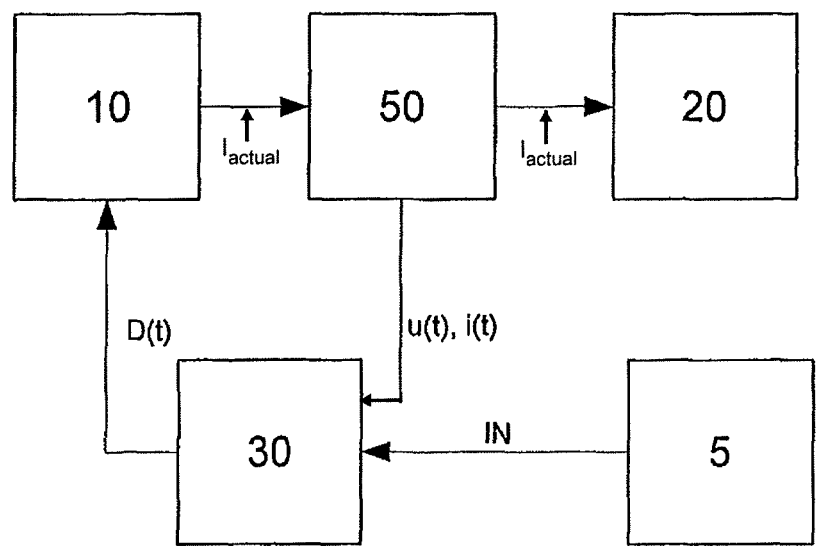
FIG. 1 shows the basic components of an electrosurgical device according to a disclosed embodiment.

FIG. 1 shows the essential components of an electrosurgical instrument. These comprise an operating unit 5 for activating and selecting a cutting and/or coagulation mode, an electrosurgical instrument 20 for applying an HF treatment current $I_{actual}$, an HF generator 10 for generating the HF treatment current $I_{actual}$, a measuring device 50 for generating a current signal i(t) and a voltage signal u(t) from the HF treatment current generated $I_{actual}$ and a control device 30 for controlling the HF generator 10.

Seen as a whole, at a time point t, the HF generator 10 provides a treatment current $I_{actual}$ at an actual voltage $U_{actual}$, with which the electrosurgical instrument 20 is operated. From this value, the measuring device 50 determines the characteristic current signals i(t) and voltage signals u(t) for this apparent power S. The control device 30 processes the current signal i(t) and the voltage signal u(t) as well as the operator signals IN, which are input by the user of the electrosurgical instrument 20 with the operating unit 5. Based on these signals, the control device 30 determines corresponding control signals D(t), by means of which the HF generator 10 is adjusted. These control signals D(t) comprise a voltage control signal $U_{target}$. In order to enable appropriate control of the HF generator 10, the control device 30 comprises a processor which is configured to carry out various operations for processing the current signal i(t) and the voltage signal u(t), and a corresponding memory device which enables results and/or settings and/or other data to be stored in the short term or lastingly. The control device 30 is therefore configured, inter alia, to implement the regulator 31 described below and a corresponding regulating loop.

Figure 2:
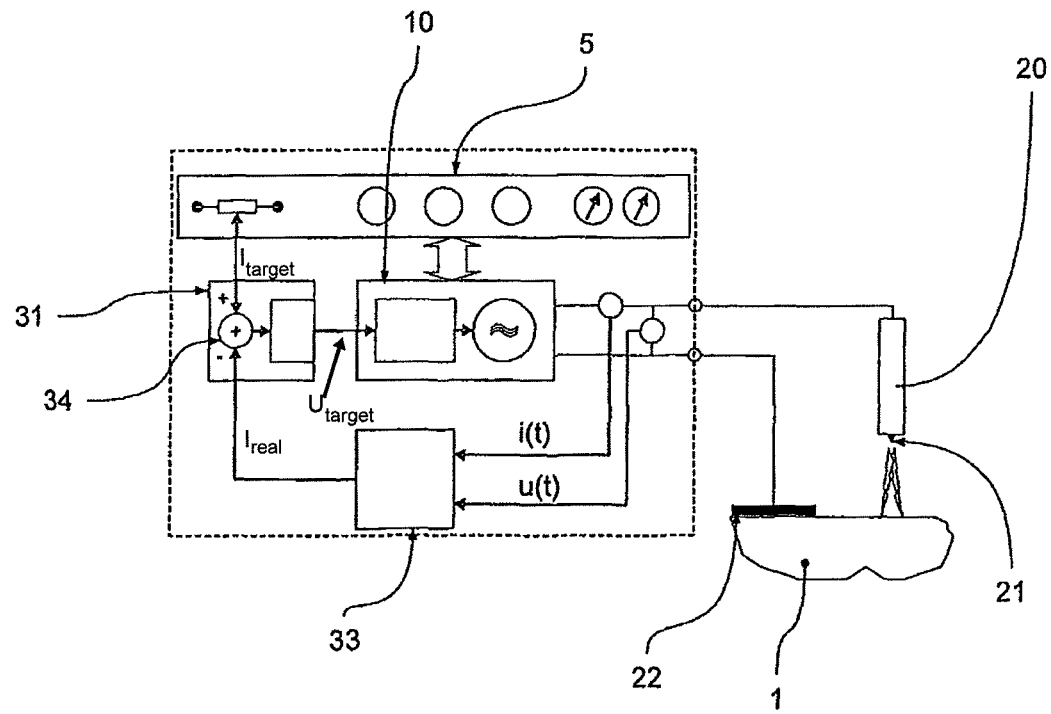
FIG. 2 shows a schematic representation of a regulating system of the electrosurgical device according to a disclosed embodiment.

FIG. 2 shows, in schematic form, a regulating loop which is used for control of the HF generator 10 according to the invention. The HF generator 10 operates a monopolar electrosurgical instrument 20, which is connected thereto via a first line. The electrosurgical instrument 20 comprises a first electrode 21 for applying an HF treatment current $I_{actual}$. The second electrode 22, which is also connected via a line to the HF generator 10 lies directly against the tissue 1 to be treated. This is a neutral electrode which creates a large area contact with the tissue 1 to be treated or the body of the patient.

During operation of the regulating system, a target value of the real current $I_{target}$ is pre-set by the operating unit 5. A regulator 31 determines a voltage control signal $U_{target}$ from this target value of the real current $I_{target}$ and from a real current $I_{real}$ by means of a comparator or an error amplifier 34. The HF generator 10 applies a corresponding voltage to the electrodes 21, 22. This produces a treatment current $I_{actual}$. The measuring device 50 detects the current signal i(t) and the voltage signal u(t) and determines a real current $I_{real}$ by means of a real current calculation unit 33. The real current $I_{real}$ is compared, as previously mentioned, in said error amplifier 34, with the set target value of the treatment current $I_{target}$ and is converted into a corresponding voltage control signal $U_{target}$. This voltage control signal $U_{target}$ is fed to the HF generator 10 as previously described. A regulating loop therefore comes into being which continuously determines the real current $I_{real}$ from the HF treatment current $I_{actual}$ and adjusts the voltage control signal $U_{target}$ such that the value of the difference between the real current $I_{real}$ and the target value of the real current $I_{target}$ is as small as possible.

A substantial part of the present disclosure lies in determining, in a precise and error-tolerant manner, the real current $I_{real}$ or, more generally expressed, the ratio between the real power P and the reactive power Q of the above-described system. For this purpose, four different methods are described below.

Calculation of the real current $I_{real}$ initially involves the formation of a power factor cos φ, which puts the real current $I_{real}$ and the apparent current $I_{apparent}$ in relation to each another. In the exemplary embodiment above, the apparent current $I_{apparent}$ corresponds to the treatment current $I_{actual}$. Therefore:

$$I_{real} = I_{apparent} \cos \phi \quad \text{(formula 1)}$$

According to the power triangle, the following relation exists between real power P, reactive power Q and apparent power S:

$$S = \sqrt{P^2 + Q^2} \quad \text{(formula 2)}$$

Figure 3:
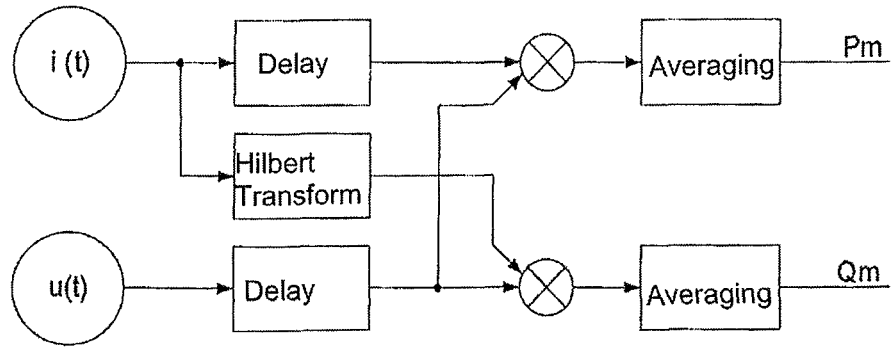
FIG. 3 shows a first method (Hilbert operation) for determining the real power and the reactive power from a current signal and a voltage signal according to a disclosed embodiment.

In a first exemplary embodiment, in order to calculate the real power P and the reactive power Q, the Hilbert transform is used (see FIG. 3). The known Hilbert transform causes a frequency-independent and amplitude-neutral phase shift of time signals by 90°. However, as far as the further processing of the signal is concerned, it is important that the digital Hilbert operator, which is implemented as an FIR filter, has a throughput time that is typical of FIR structures. It is therefore important that chronologically associated values of current and voltage are always processed together. In the first exemplary embodiment, a reactive power mean value $Q_m$ is determined by the use of the Hilbert operator on the time-dependent current signal i(t) and subsequent multiplication by the delayed voltage signal u(t). The mean value of the reactive power Q, i.e. the reactive power mean $Q_m$, can be obtained by averaging over at least one voltage waveform period or current waveform period. Calculation of the real power mean $P_m$ is carried out by direct multiplication of the current signal i(t) by the voltage signal u(t), wherein, here also, averaging takes place over at least one period.

By evaluating the relationships in the right-angle power triangle (apparent power S is the hypotenuse, real power P is the adjacent side and Q is the opposite side to the angle φ), the power factor cos φ can be calculated by the following two methods (see also formula 1):

$$\cos\varphi = \cos\left(\arctan\left(\frac{Q_m}{P_m}\right)\right) \quad \text{(formula 3)}$$

$$\cos\varphi = \frac{P_m}{\sqrt{P_m^2 + Q_m^2}} \quad \text{(formula 4)}$$

The control system 30 described can therefore calculate the real current $I_{real}$ using the Hilbert transform and by means of the formulae 1 and 3 or 1 and 4.

Figure 4:
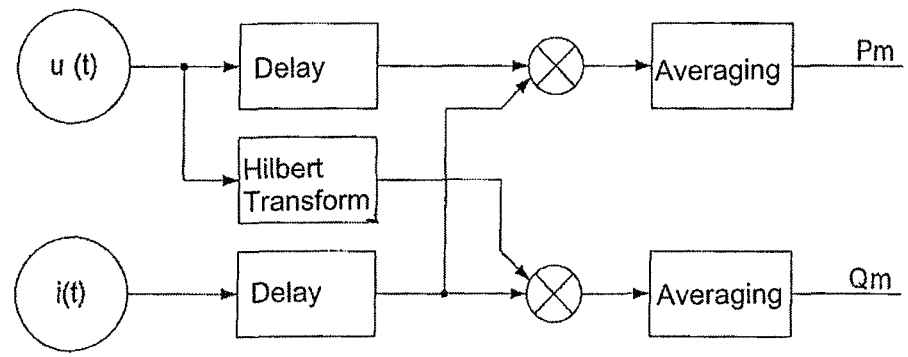
FIG. 4 shows a second method (Hilbert operation) for determining the real power and the reactive power from a current signal and a voltage signal according to a disclosed embodiment.

A second method for calculating the real power P and the reactive power Q can also be provided using the Hilbert transform (see FIG. 4). In this case, the voltage signal u(t) is transformed and multiplied by the delayed current signal i(t). The reactive power mean value $Q_m$ is found by averaging the values calculated in this way. The real power mean value $P_m$ is found by multiplication of the current signal i(t) by the voltage signal u(t) and subsequent averaging of the values.

Using the reactive power mean $Q_m$ and the real power mean $P_m$, the power factor cos φ can be determined with the above formula, so that a relation can be established between the real current $I_{real}$ and the apparent current $I_{apparent}$.

Figure 5:
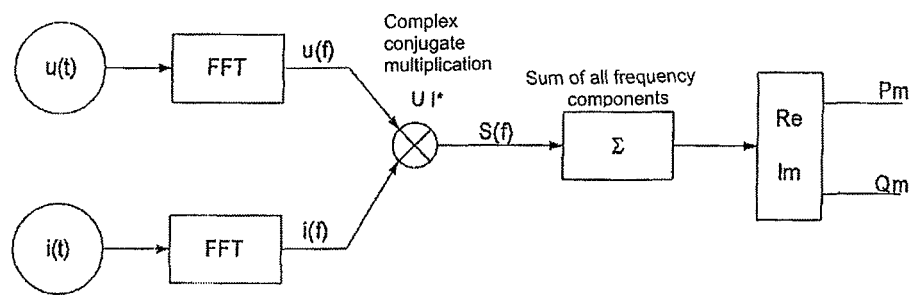
FIG. 5 shows a third method (FFT) for determining the real power and the reactive power from a current signal and a voltage signal according to a disclosed embodiment.

A third method for determining the real power P is as shown in FIG. 5. Firstly, the current signal i(t) and the voltage signal u(t) are subjected to a discrete or fast Fourier transform (DFT, FFT). In order to minimise the calculation effort required, an FFT is preferably selected as illustrated in FIG. 5. As the result of the FFT, a vector of complex number values is obtained, comprising real and imaginary components of the current signal i(t).

Following complex conjugate multiplication, the power is given, separated into real component (P) and reactive portion (Q) as follows:

$$\underline{U} \cdot \underline{I}^* = |U|e^{j\phi_u} \cdot |I|e^{-j\phi_i} = |U| \cdot |I|e^{-j(\phi_u - \phi_i)} = P + jQ \quad \text{(formula 5)}$$

By totaling the vector values of the real power P and by a separate totaling of the reactive power Q, the real power mean $P_m$ and the reactive power mean $Q_m$ are obtained. The power factor cos φ can be determined as described above by using the formulae 3 or 4.

According to the disclosure, there are two methods for determining the apparent current $I_{apparent}$. The value of the apparent current $I_{apparent}$ can be found from the complex results of the FFT by absolute value formation:

$$I_{apparent} = \sum_{all\,frequency\,portions} |i_r + j \cdot i_i| = \sum_{all\,frequency\,portions} \sqrt{i_r^2 + i_i^2} \quad \text{(formula 6)}$$

Alternatively, totaling of the real-value instantaneous values of the current over a period can be undertaken.

In a fourth method, the real current P can be determined from the effective values of current $i_{eff}$ and voltage $u_{eff}$. For sinusoidal current and voltage forms, the real power P is defined by means of the power factor $\cos \phi$ as follows:

$$P = u_{eff} \cdot i_{eff} \cos \phi \quad \text{(formula 7)}$$

If the real power P is replaced with the real power mean $P_m$, then the power factor $\cos \phi$ can be determined from the real power mean $P_m$ and the effective values of the current and voltage variations i(t), u(t). Thus, for the power factor $\cos \phi$ the following then applies:

$$\cos \varphi = \frac{P_m}{u_{eff} \cdot i_{eff}} \quad \text{(formula 8)}$$

A calculation of the real power mean value $P_m$ can be carried out for N sample values as follows:

$$P = \frac{1}{N} \sum_{k=1}^{N} u(k) \cdot i(k) \quad \text{(formula 9)}$$

The effective value $u_{eff}$ of the voltage is found, over N sample values, from the equation which defines it:

$$u_{eff} = \frac{1}{N} \sqrt{\sum_{k=1}^{N} (u(k))^2} \quad \text{(formula 10)}$$

In a similar way, the effective value of the current $i_{eff}$ can be found:

$$i_{eff} = \frac{1}{N} \sqrt{\sum_{k=1}^{N} (i(k))^2} \quad \text{(formula 11)}$$

Making use of the power factor $\cos \phi$ thus obtained, the real component of the current is found from:

$$i_{wirk,eff} = i_{eff} \cos \phi \quad \text{(formula 12)}$$

The last method is characterised, in particular, by the fact that relatively few operations have to be performed to determine the real current $I_{real}$. However, using modern digital signal processing electronics, methods 1 to 3 can also be implemented.

The invention claimed is:

1. An electrosurgical generator for the coagulation of biological tissue by means of an inert gas plasma coagulation instrument, comprising
  a generator part which supplies a high-frequency treatment current with a high-frequency voltage set according to a voltage control signal such that electrical energy is supplied to the biological tissue;
  a measuring device for detecting the high-frequency treatment current and the high-frequency voltage for generating a corresponding current signal and a corresponding voltage signal;
  a conversion device to which the current signal and the voltage signal are fed and which is configured such that a real current signal corresponding to the real component of the high-frequency treatment current is formed from the current signal and the voltage signal; and
  a regulation device which compares the real current signal with a pre-settable target value and generates the voltage control signal on the basis of the comparison, wherein the real component of the high-frequency treatment current is adjustable according to the target value for ensuring a tissue treatment that is independent of a distance between the tissue and an electrode of the inert gas plasma coagulation instrument when performing a contactless coagulation procedure.

2. The electrosurgical generator according to claim 1, further comprising a power limiting device which determines a real power based on the current signal and the voltage signal and limits said real power to a pre-set value.

3. The electrosurgical generator according to claim 1, further comprising a current limiting device which limits the real component of the treatment current to a pre-set value.

4. The electrosurgical generator according to claim 1, further comprising a data input and data storage device for input and storage of real resistance components and reactive impedance components of attached surgical instruments and loads, wherein the data input and data storage device is connected to the conversion device, wherein the conversion device is configured to include the reactive impedance portions when calculating the real component of the high-frequency treatment current.

5. The electrosurgical generator according to claim 1, wherein the conversion device comprises a computer device which forms the real current signal using one of:
  a Hilbert transform,
  a discrete Fourier transform,
  a fast Fourier transform, and
  a determination of mean power from N sample values and a determination of effective values of voltage and current, where mean power P is determined according to the equation $$P = \frac{1}{N} \sum_{k=1}^{N} u(k) \cdot i(k)$$

where N is a positive integer, u(k) is the voltage signal at sample k, and i(k) is the current signal at sample k, and where effective values of voltage $u_{eff}$ and current $i_{eff}$ are determined according to the equations $$u_{eff} = \frac{1}{N} \sqrt{\sum_{k=1}^{N} (u(k))^2}$$

$$i_{eff} = \frac{1}{N} \sqrt{\sum_{k=1}^{N} (i(k))^2}$$

wherein the real current signal $i_{real,eff}$ is given by $$i_{real,eff} = i_{eff} \cos \phi$$

where $$\cos \varphi = \frac{P}{u_{eff} \cdot i_{eff}}.$$

6. A method for regulating an output voltage of an electrosurgical generator which supplies a high-frequency treatment current at a high-frequency voltage for the coagulation of biological tissue by means of an inert gas plasma coagulation instrument, comprising the steps:

detecting the high-frequency treatment current and the high-frequency voltage and generating a corresponding current signal and a corresponding voltage signal;

forming a real component of the high-frequency treatment current from the current signal and the voltage signal and generating a corresponding real current signal;

comparing the real current signal with a pre-settable target value and generating a voltage control signal based on the comparison; and regulating the output voltage such that the real component of the high-frequency treatment current corresponds to the target value, wherein the real component of the high-frequency treatment current is adjustable according to the target value for ensuring reliable ignition of an inert gas plasma of the inert gas plasma coagulation instrument when performing a contactless coagulation procedure.

7. The method according to claim 6,
wherein the real current signal is formed using one of:
a Hilbert transform,
a discrete Fourier transform,
a fast Fourier transform, and
a determination of mean power from N sample values and a determination of effective values of voltage and current, where mean power P is determined according to the equation $$P = \frac{1}{N}\sum_{k=1}^{N} u(k) \cdot i(k)$$

where N is a positive integer, u(k) is the voltage signal at sample k, and i(k) is the current signal at sample k, and where effective values of voltage $u_{eff}$ and current $i_{eff}$ are determined according to the equations $$u_{eff} = \frac{1}{N}\sqrt{\sum_{k=1}^{N}(u(k))^2}$$

$$i_{eff} = \frac{1}{N}\sqrt{\sum_{k=1}^{N}(i(k))^2}$$

wherein the real current signal $i_{real,eff}$ is given by $$i_{real,eff} = i_{eff} \cdot \cos\varphi$$

where $$\cos\varphi = \frac{P}{u_{eff} \cdot i_{eff}}$$

8. A system for treatment of biological tissue, comprising:
an inert gas plasma coagulation instrument for the coagulation of biological tissue; and
an electrosurgical generator comprising:
a generator part which supplies a high-frequency treatment current with a high-frequency voltage set according to a voltage control signal such that electrical energy is supplied to the biological tissue;
a measuring device for detecting the high-frequency treatment current and the high-frequency voltage for generating a corresponding current signal and a corresponding voltage signal;
a conversion device to which the current signal and the voltage signal are fed and which is configured such that a real current signal corresponding to the real component of the high-frequency treatment current is formed from the current signal and the voltage signal; and
a regulation device which compares the real current signal with a pre-settable target value and generates the voltage control signal on the basis of the comparison,
wherein the real component of the high-frequency treatment current is adjustable according to the target value for ensuring a tissue treatment that is independent of a distance between the tissue and an electrode of the inert gas plasma coagulation instrument when performing a contactless coagulation procedure.

9. The system according to claim 8, wherein the electrosurgical generator further comprises a power limiting device which determines a real power based on the current signal and the voltage signal and limits said real power to a pre-set value.

10. The system according to claim 8, wherein the electrosurgical generator further comprises a current limiting device which limits the real component of the treatment current to a pre-set value.

11. The system according to claim 8, wherein the electrosurgical generator further comprises a data input and data storage device for input and storage of real resistance components and reactive impedance components of attached surgical instruments and loads, wherein the data input and data storage device is connected to the conversion device, wherein the conversion device is configured to include the reactive impedance portions when calculating the real component of the high-frequency treatment current.

12. The system according to claim 8, wherein the conversion device comprises a computer device which forms the real current signal using one of:
a Hilbert transform,
a discrete Fourier transform,
a fast Fourier transform, and
a determination of mean power from N sample values and a determination of effective values of voltage and current, where mean power P is determined according to the equation $$P = \frac{1}{N}\sum_{k=1}^{N} u(k) \cdot i(k)$$

where N is a positive integer, u(k) is the voltage signal at sample k, and i(k) is the current signal at sample k, and where effective values of voltage $u_{eff}$ and current $i_{eff}$ are determined according to the equations $$u_{eff} = \frac{1}{N}\sqrt{\sum_{k=1}^{N}(u(k))^2}$$

$$i_{eff} = \frac{1}{N}\sqrt{\sum_{k=1}^{N}(i(k))^2}$$

wherein the real current signal $i_{real,eff}$ is given by $$i_{real,eff} = i_{eff} \cdot \cos\varphi$$

where $$\cos\varphi = \frac{P}{u_{eff} \cdot i_{eff}}.$$

* * * * *